US009475853B2

(12) United States Patent
Hazlett et al.

(10) Patent No.: US 9,475,853 B2
(45) Date of Patent: Oct. 25, 2016

(54) FUSION PROTEIN FOR ENHANCING IMMUNOGENICITY OF BACTERIAL ANTIGEN/IMMUNOGEN

(71) Applicant: ALBANY MEDICAL COLLEGE, Albany, NY (US)

(72) Inventors: Karsten Hazlett, East Berne, NY (US); Edmund Gosselin, Glenmont, NY (US); Timothy Sellati, Saranac Lake, NY (US); Tiffany Zarrella, Albany, NY (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 0 days.

(21) Appl. No.: 14/373,212

(22) PCT Filed: Jan. 22, 2013

(86) PCT No.: PCT/US2013/022526
§ 371 (c)(1),
(2) Date: Jul. 18, 2014

(87) PCT Pub. No.: WO2013/110064
PCT Pub. Date: Jul. 25, 2013

(65) Prior Publication Data

US 2015/0030632 A1 Jan. 29, 2015

Related U.S. Application Data

(60) Provisional application No. 61/588,368, filed on Jan. 19, 2012, provisional application No. 61/681,996, filed on Aug. 10, 2012.

(51) Int. Cl.

| | |
|---|---|
| ***A61K 39/02*** | (2006.01) |
| ***C07K 14/47*** | (2006.01) |
| ***C07K 14/195*** | (2006.01) |
| *A61K 39/00* | (2006.01) |

(52) U.S. Cl.
CPC ......... *C07K 14/472* (2013.01); *A61K 39/0208* (2013.01); *A61K 39/0291* (2013.01); *C07K 14/195* (2013.01); *A61K 2039/53* (2013.01); *A61K 2039/6031* (2013.01); *C07K 2319/00* (2013.01); *C07K 2319/33* (2013.01)

(58) Field of Classification Search
None
See application file for complete search history.

(56) References Cited

FOREIGN PATENT DOCUMENTS

| | | | |
|---|---|---|---|
| WO | 9617625 | A1 | 6/1996 |
| WO | 2008048289 | A2 | 4/2008 |

OTHER PUBLICATIONS

Sjostedt A et al; Humoral and Cell-Mediated Immunity in Mice to a 17-Kilodalton Lipoprotein of Francisella-Tularensis Expressed by *Salmonella-typhimurium*, Infection and Immunity, American Society for Microbiology, USA, vol. 60, No. 7, Jan. 1, 1992.

Shalini Thakran et al; "Identification of Francisella tularensis lipoproteins that stimulate the toll-like receptor (TLR)2/TLR1 heterodimer," Journal of Biological Chemistry, American Society for Biochemistry and Molecular Biology, US, vol. 283, No. 7, Feb. 15, 2008.

Ben Nasr Abdelhakim et al; "Subversion of complement activation at the bacterial surface promotes serum resistance and opsonophagocytosis of Francisella tularensis," Journal of Leukocyte Biology, vol. 84, No. 1, Jul. 2008.

International Search Report for PCT/US2013/022526 dated May 29, 2013.

*Primary Examiner* — Brian J Gangle
(74) *Attorney, Agent, or Firm* — Heslin Rothenberg Farley & Mesiti P.C.; Kathy Smith Dias

(57) ABSTRACT

Establishment of an effective and uniform vaccine development strategy is key to conquering current and emerging infectious diseases. Despite successes against an array of bacterial agents, current approaches to vaccine development are as diverse as the microbes they target and require adjuvants that often have limited efficacy and/or toxic side effects. As a consequence, vaccine discovery is often slow, inefficient, and unsuccessful in the case of many high priority pathogens. The present disclosure suggests that vaccine generation for bacterial pathogens can be improved by optimizing the efficiency of processing/presentation of a bacterial immunogen via the targeting of immunogen to CR2 and/or TLR2 on APCs. This approach not only yields an adjuvant-free mucosal vaccine against a Category A biothreat agent, but also establishes a novel genetic approach/platform for vaccine development, which is applicable to many other infectious agents, thereby profoundly impacting preventive medicine/public health.

27 Claims, 6 Drawing Sheets

FUSION PROTEIN FOR ENHANCING IMMUNOGENICITY OF BACTERIAL ANTIGEN/IMMUNOGEN

CROSS REFERENCE TO RELATED APPLICATIONS

This application is a 371 National Phase of PCT International Application No. PCT/US2013/022526 filed on Jan. 22, 2013, and published in English as WO 2013/110064 A1 on Jul. 25, 2013, which claims priority to U.S. provisional application Ser. Nos. 61/588,368, filed Jan. 19, 2012 and 61/681,996, filed Aug. 10, 2012. The contents of these disclosures are hereby incorporated by reference into the present application.

GOVERNMENT RIGHTS STATEMENT

This invention was made with U.S. Government support under grant no. PO1-AI056320 awarded by the NIAID of the National Institutes of Health. The U.S. Government has certain rights in the invention.

SEQUENCE LISTING

This application contains a Sequence Listing, created on Jan. 15, 2013; the file, in ASCII format, is designated 0410046AWO_sequencelisting_ST25.txt and is 13.8 kilobytes in size. The sequence listing file is hereby incorporated by reference in its entirety into the application.

TECHNICAL FIELD

The present disclosure relates generally to vaccine development. More particularly, the present disclosure relates to a polynucleotide construct that enhances immunogenicity of a bacterial pathogen transformed with the construct.

BACKGROUND OF THE DISCLOSURE

*Francisella tularensis* (Ft)) is a Gram-negative, facultative intra-cellular pathogen and the etiological agent of tularemia, a disease that can be fatal in humans. Ft can infect individuals at both mucosal and peripheral sites, with the former being the most lethal form of infection. Both humoral and cellular immunity play a role in protection against this organism. While there are only about 200 known Ft infections per year in the U.S., as few as one organism can be fatal, if inhaled. This has led to the obvious concern that Ft could be used as a bioterrorism agent, when dispersed as an aerosol in a populated area. Thus, Ft has been listed as a category A select agent, and there is strong interest in the development of an effective vaccine against Ft.

Furthermore, the development of needle-free, mucosal vaccines that do not require exogenous adjuvants is of significant interest to all areas of infectious disease including biodefense. Even though some infections can be treated successfully with antibiotics, under some circumstances, such as biodefense, vaccination is preferred over post-exposure therapy.

To date, the current gold standard for tularemia prophylaxis, infection with viable Live Vaccine Strain (LVS) Ft, provides only moderate protection in humans. Thus, a need exists for a vaccine that yields improved efficacy and a major effort is underway to develop a new generation of safe and effective vaccines against the disease.

SUMMARY OF THE DISCLOSURE

The present disclosure is directed to fusion proteins and nucleic acids encoding those fusion proteins, which, when expressed in a pathogenic bacterial cell that is administered to a subject, significantly enhances immune responsiveness in the subject to the pathogen.

In one aspect, therefore, the disclosure relates to fusion proteins and nucleic acids that encode the fusion proteins, the fusion protein comprising a *Francisella tularensis* (Ft) lipoprotein such as Tul4A that binds toll-like receptor 2 (TLR2) linked to a portion of complement component 3 (C3), such as C3d, that binds to a complement receptor type 2 (CR2) on immune effector cells. The nucleic acid(s) may be part of a polynucleotide that comprises an expression cassette, that is, it may be part of a construct that includes a promoter and/or other regulatory elements that effect expression. Vectors which include the nucleic acid and/or an expression cassette containing the nucleic acid are encompassed by the disclosure.

In another aspect, therefore, the disclosure relates to a polynucleotide, for example, a vector comprising a nucleic acid that encodes a fusion protein comprising a Ft lipoprotein that binds toll-like receptor 2 (TLR2) such as Tul4A linked to C3d. The nucleic acid encoding the fusion protein or expression cassette incorporating the nucleic acid encoding the fusion protein can be cloned into a variety of plasmids to achieve expression of the fusion protein in a wide range of bacteria.

In yet another aspect, the disclosure relates to a bacterial cell that has been transformed using a vector comprising a nucleic acid encoding a fusion protein of a Ft lipoprotein that binds toll-like receptor 2 (TLR2) such as Tul4A linked to C3d. The transformed bacterial cell expressing the fusion p In a related aspect, the disclosure relates to a pharmaceutical composition comprising a bacterial cell that has been transformed with a vector comprising a nucleic acid encoding a fusion protein of Tul4A linked to C3d. The transformed bacterial cell expresses the fusion protein, which is anchored to the outer membrane of the bacteria.

DETAILED DESCRIPTION OF THE DISCLOSURE

Figure 1:
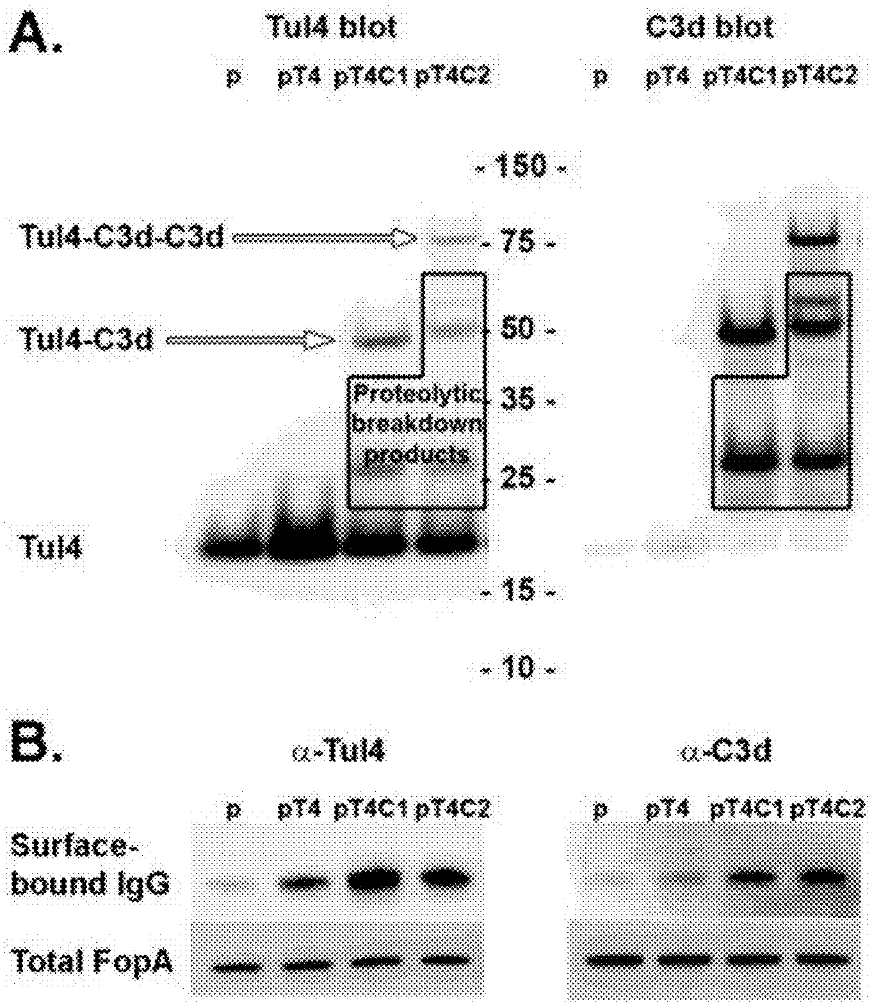
FIG. 1A-B shows expression and surface-exposure of Tul4A and C3d by engineered Ft LVS. A) Ft strains harboring either the empty vector (p), the Tul4A over-expression vector (pT4), or the Tul4A-C3d vectors (pT4C1 and pT4C2) were probed by western blot for total Tul4A and C3d. In B, intact bacteria were incubated with α-Tul4A or α-C3d Ab, washed, and probed by western blot for IgG heavy chain as an indication of surface-exposed Tul4A or C3d. The blot was subsequently stripped and re-probed for total FopA as a loading control.

All patents, published applications and other references cited herein are hereby incorporated by reference in their entirety.

In practicing the present disclosure, many conventional techniques in microbiology, molecular biology and immunology are used, which are within the skill of the ordinary artisan. Some techniques are described in greater detail in, for example, Molecular Cloning: a Laboratory Manual 3rd edition, J. F. Sambrook and D. W. Russell, ed. Cold Spring Harbor Laboratory Press 2001, the contents of this and other references containing standard protocols, widely known to and relied upon by those of skill in the art, including manufacturers' instructions are hereby incorporated by reference as part of the present disclosure.

Abbreviations used herein include the following:

APCs: antigen presenting cells

BMDCs: bone marrow dendritic cells

BMDM: bone-marrow-derived macrophages

C3d: complement component 3 fragment d

FDCs: follicular dendritic cells

Ft: *Francisella tularensis*

Ft LVS: *F. tularensis* live vaccine strain

TLR2: toll-like receptor 2

Tul4A: a *F. tularensis* membrane lipo-protein; also known as LpnA or FTT0901.

Yp: *Yersinia pestis*

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure. All publications, patent applications, patents, and other references mentioned herein are incorporated by reference in their entirety.

The term "fusion polypeptide" or "fusion protein" refers to a protein having at least two heterologous polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. The term encompasses conservatively modified variants, polymorphic variants, alleles, mutants, subsequences, interspecies homologs, and immunogenic fragments of the antigens that make up the fusion protein. Fusion proteins of the disclosure can also comprise additional copies of a component antigen or immunogenic fragment thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. An expression cassette can be designed to include or delete transcription termination signals, enhancers, and other nucleic acid sequences that influence gene expression to achieve a desired expression product. In some embodiments, a recombinant expression cassette encoding an amino acid sequence for a fusion protein of the disclosure is expressed in a bacterial host cell.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The term "linker" or "linked" refers to the covalent linkage between two polypeptides in a fusion protein. The polypeptides are typically joined via a peptide bond, either directly to each other or via one or more additional amino acids. The composition and length of the linker may be determined in accordance with methods well known in the art and may be tested for efficacy. The linker is generally from about 3 to about 15 amino acids long, in some embodiments about 5 to about 10 amino acids long, however, longer or shorter linkers may be used or the linker may be dispensed with entirely. A glycine linker is one that contains one or more glycines but no other amino acids, e.g. GGGG (SEQ ID NO: 14). A glycine-rich linker is one that contains one or more glycines and may contain other amino acids as long as glycine is the predominant species in the linker e.g. GGGNGG (SEQ ID NO: 13). A glycine-serine linker is one which contains both glycine and serine in any proportion, e.g. GGGS (SEQ ID NO: 11).

The term "adjuvant" refers to the components in a vaccine or therapeutic composition that increase the specific immune response to the antigen (see, e.g., Edelman, AIDS Res. Hum Retroviruses 8:1409-1411 (1992)). Adjuvants are well known to those of skill in the art and may include cytokines (e.g., IFN-γ, IL-2, and IL-12) which contribute to the induction of cell-mediated immune response to an administered antigen, as well as induction of humoral immune responses.

The terms "nucleic acid" and "polynucleotide" refer to deoxyribonucleotides and polymers thereof.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with cDNA, mRNA, oligonucleotide, and polynucleotide.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

The terms "polypeptide," and "protein" are used interchangeably herein to refer to a polymer of amino acid residues. The terms encompass amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The present disclosure is based, in part, on the observation that the expression by a bacterium of a fusion protein combining a TLR2 ligand (e.g. Tul4A) and a complement receptor ligand (e.g. C3d), can (1) increase binding of the bacterium by cells bearing CR2 such as B-cells or FDCs; and (2) increase survival of animals that were immunized with bacteria bearing the fusion protein on their surface prior to challenge with the bacteria. The fusion protein disclosed herein, therefore, enhances immunogenicity of a whole bacteria immunogen when the fusion protein is expressed at the surface, thereby boosting the immune response mounted in a subject against that bacteria.

Without wishing to be bound by theory, the expression of a Tul4A-C3d(n) fusion protein of the disclosure by a bacterial cell enhances the immunogenicity of that bacterial immunogen by targeting of the bacteria (inactivated for example) to host cells bearing the complement receptor CR2 while at the same time stimulating TLR2 on the same host immune effector cells at an increased level due to the overexpression of Tul4A. This results in highly-efficient delivery of the immunogen (the bacteria expressing Tul4A-C3d(n)) to the most potent antigen-presenting cells that, by virtue of TLR2 stimulation, should become highly activated to initiate a robust immune response.

Tul4A is an integral membrane lipoprotein expressed across different strains of *Francisella*. In engineering bacterial cells that express a Tul4A-C3d(n) fusion protein, transformation with a nucleic acid of the invention encodes a fusion protein that is not secreted but membrane-bound.

Tul4A binds to the host toll-like receptor 2 (TLR2) to activate cells bearing this receptor. Expression of a TUL4A-C3d(n) fusion protein increases the concentration of Tul4A on the surface of the bacterial cell; Tul4A acts as a protein adjuvant for antigen (Ag)—presenting cells (APCs). Additionally, TLR2 ligands may also target delivery of antigens to these APCs.

C3d is a fragment of mammalian complement component 3 which binds the complement receptor 2 (CR2) expressed on B-cells and follicular dendritic cells (FDCs); i.e. C3d targets CR2 for delivery of C3d-linked moieties to B-cells and FDCs. Linking Tul4A-C3d fusion proteins to whole cell immunogens targets delivery of the immunogen to CR2-positive cells (and potentially TLR2-positive cells) and stimulate a potent anti-immunogen response through TLR2-stimulation. Since the immunogen is targeted (via C3d) and adjuvantized (via Tul4A), the need for external adjuvants should be reduced/eliminated.

Plasmids

In one embodiment, coding regions of the *Francisella tularensis* (Ft) gene encoding Tul4A (a surface-exposed lipoprotein) (Genbank accession no. FTT0901) were genetically fused in-frame with DNA encoding residues 1024-1320 from murine C3. C3 encoding DNA was PCR amplified from plasmid pMLC3/7 (ATCC, Manassas, Va.) and fused in-frame to the 3' end of either Tul4A or PilA (the SchuS4-specific pilin subunit protein.) This portion of murine C3 is 91% identical to human C3d. Both of these Ft genes lack a stop codon to allow for the production of Tul4A-C3d and/or PilA-C3d fusion proteins.

In some embodiments, constructs which encode multiple copies of C3d (these are designated C3d(n) where n=an integer from 1 to 5) downstream of Tul4A are desirable; these were developed to increase the avidity of the Tul4A-C3d(n) chimeras for CR2.

In one embodiment, the chimeric gene is placed downstream of a promoter, such as a groEL promoter and the groEL:Tul4A-C3d(n) gene fusion is moved into a plasmid(s) that will replicate and facilitate expression of the fusion protein. Useful expression vectors for bacterial hosts include bacterial plasmids, such as pBB103 and pMP633 and wider host range plasmids, such as pBAV1k-T5-gfp (Addgene, Cambridge Mass.), and pSE100 (Addgene, Cambridge Mass.). Nucleic acids encoding the fusion protein or expression cassettes incorporating the nucleic acid encoding the fusion protein can therefore, be cloned into a variety of plasmids to achieve expression of the fusion protein in a wide range of bacteria including *Francisella tularensis, Esherichia coli, Yersinia pestis, Acinetobactor baumannii, Mycobacterium tuberculosis, Borrelia burgdorferi, Methicillin*-resistant *Staphylococcus aureus, Klebsiella pneumonia*, Groups A and *B. streptococcus, Pseudomonas aeruginosa, Vancomycin*-Resistant *Enterococci, Multidrug*-Resistant *Neisseria gonorrhoeae, Helicobacter pylori*, and *Bartonella henselae.*

Figure 5:
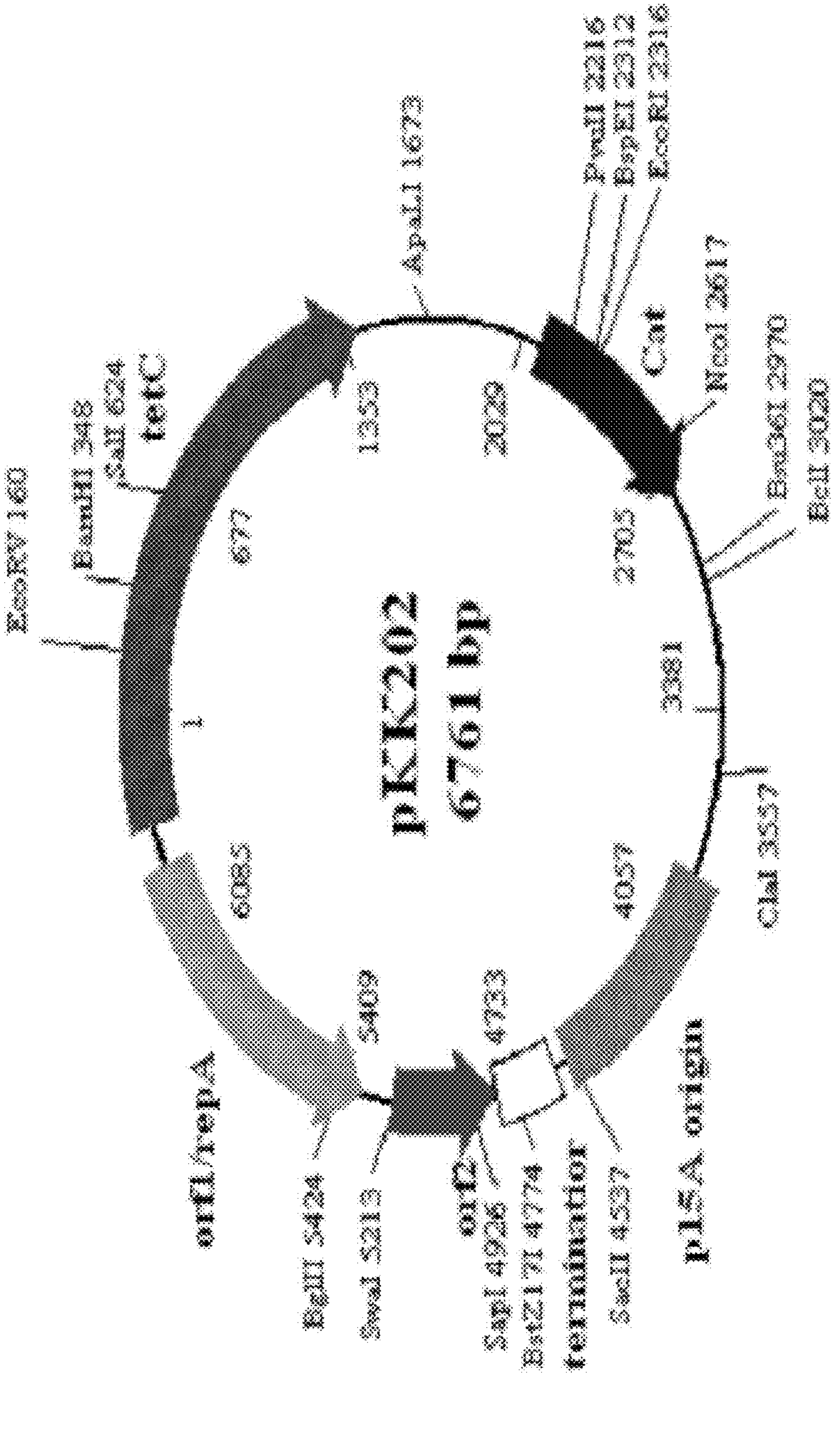
FIG. 5 is a schematic of plasmid pKK202.
Figure 6:
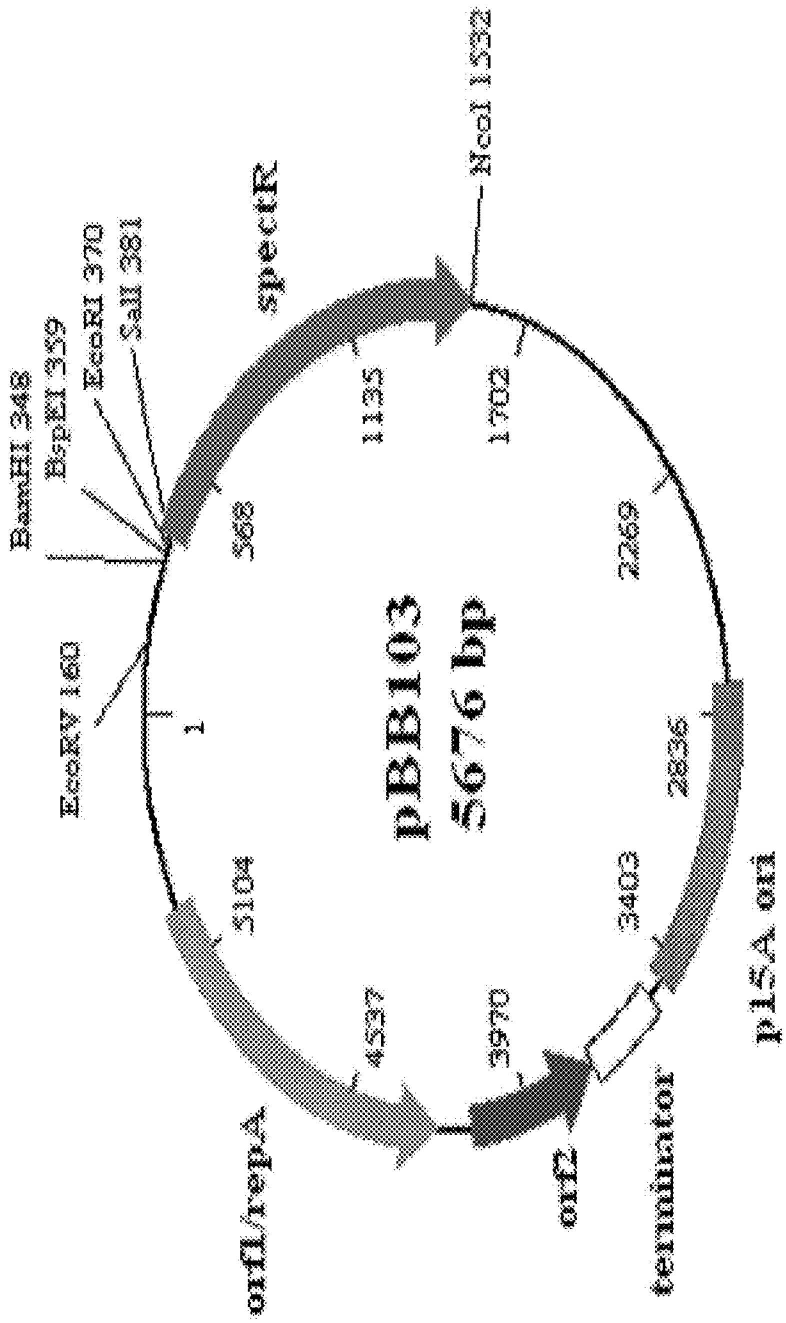
FIG. 6 is a schematic of plasmid pBB103.

In one embodiment, a plasmid, designated pBB103, was created by inserting a small MCS and the spectinomycin resistance gene into BamHI/NcoI of pKK202. This effectively replaced most of the tet and chlor resistance genes in pKK202, however, the tetC promoter remains and drives expression of whatever is cloned into the pBB103 MCS (provided it is in the same orientation as PtetC). A schematic of each of pKK202 and pBB103 is shown in FIGS. 5 and 6, respectively, and the nucleotide sequence of pBB103 is given in SEQ ID NO: 4.

*F. tularensis* (Ft) and *Y. pestis* (Yp) were transformed with a plasmid containing the expression cassette incorporating a nucleic acid sequence that encodes the fusion protein using methods known to those of skill in the art. Following transformation, Ft and Yp strains harboring either the empty vector (p), the Tul4A over-expression vector (pT4), or the Tul4A-C3d and Tul4A-C3d-C3d vectors (pT4C1 and pT4C2, respectively) were probed by western blot for total Tul4A and C3d. Intact bacteria were incubated with α-Tul4A or α-C3d antibody (Ab), washed, and probed by western blot for IgG heavy chain as an indication of surface-exposed Tul4A or C3d. The blot was subsequently stripped and re-probed for total FopA as a loading control. FIGS. 1A and 1B shows expression and surface-exposure of Tul4A and C3d by engineered Ft LVS.

Figure 4:
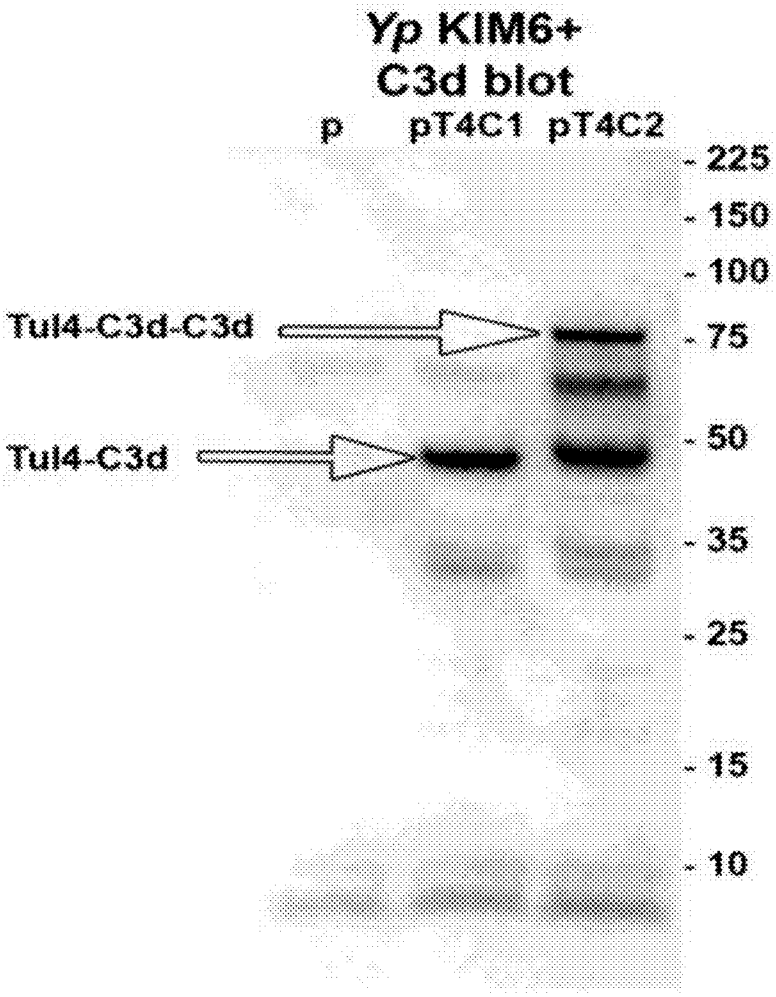
FIG. 4A-B shows expression of Tul4A-C3d(n) produced by recombinant *Yersinia pestis* (Yp). Bacterial lysates from Yp KIM6$^+$ strains harboring either the empty vector (p), or the Tul4A-C3d vectors (pT4C1+pT4C2) were resolved by SDS-PAGE and probed by western blot with antibodies which recognize the 17 kDa Ft lipoprotein Tul4AA or the 33 kDa murine complement component 3 fragment, C3d. Plasmids are designated as follows: "p" is empty vector (pBB103); "pT4" is pBB103 expressing Tul4AA; "pT4Cx" is "pT4" with one ("pT4C1") or two ("pT4C2") copies of C3d linked sequentially to the C-terminus of Tul4AA.

Yp KIM6$^+$ were similarly transformed and evaluated for expression of the fusion protein. Briefly, bacterial lysates from Yp KIM6$^+$ strains harboring either the empty vector (p), or the Tul4A-C3d vectors (pT4C1+pT4C2) were electrophoresed and probed by western blot with antibodies which recognize the 17 kDa Ft lipoprotein Tul4AA or the 33 kDa murine complement component 3 fragment, C3d. Plasmids are designated as follows: “p” is empty vector (pBB103); “pT4” is pBB103 expressing Tul4AA; “pT4Cx” is “pT4” with one (“pT4C1”) or two (“pT4C2”) copies of C3d linked sequentially to the C-terminus of Tul4AA. As shown in FIG. 4, transformation of these cells resulted in expression of Tul4A-C3d(n) by recombinant Yp.

Figure 2:
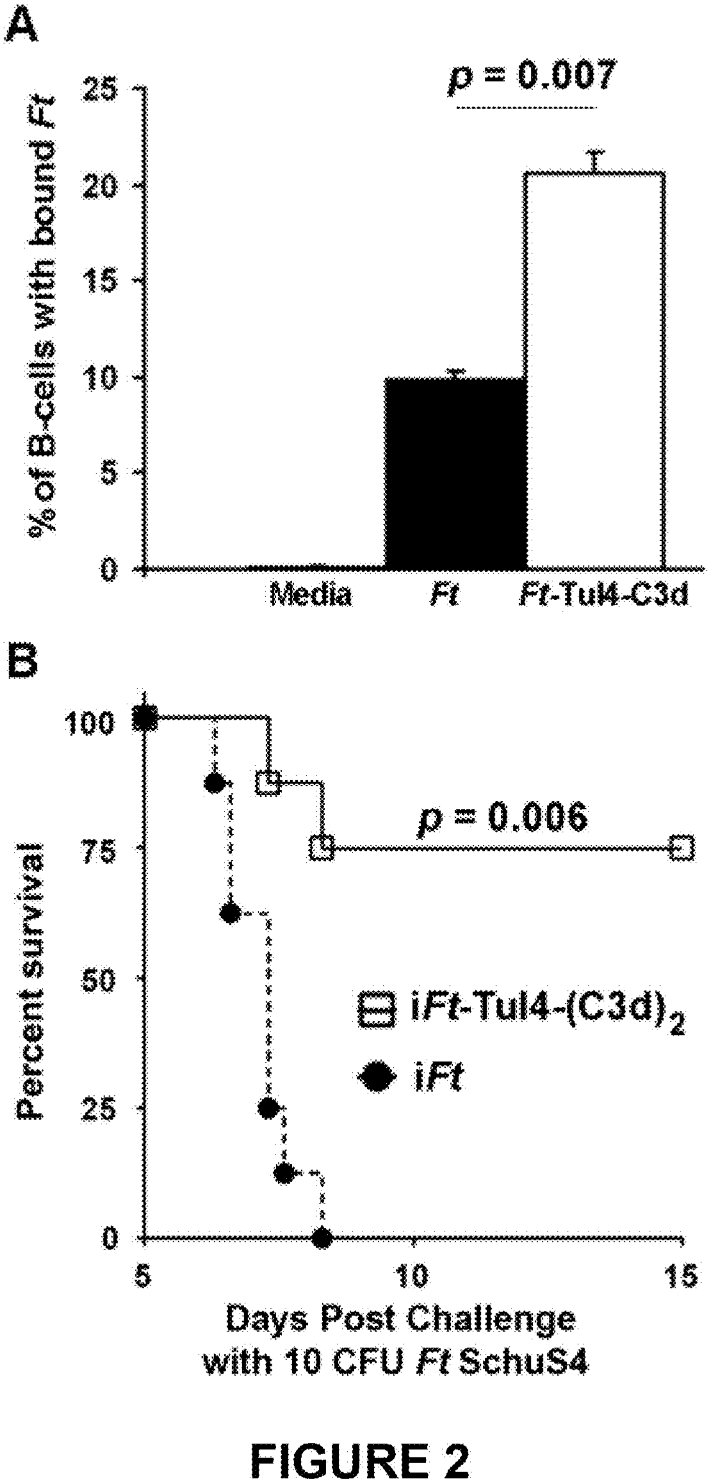
FIG. 2 shows that engineered expression of Tul4A-C3d by Ft promotes binding to CR2-expressing cells. CR2-positive B cells (A20 cells) were incubated for 2 hrs with media or fluorescently-labeled (pKH26-treated) Ft LVS strains. Following fixation and washing, the B cells were analyzed by flow cytometry.

Next, to determine whether bacteria bearing the Tul4A-C3d/Tul4A-C3d-C3d fusion protein would be bound by B cells, CR2-positive B cells (A20 cells) were incubated for 2 hrs with media or fluorescently-labeled (pKH26-treated) Ft LVS strains. Following fixation and washing, the B cells were analyzed by flow cytometry. FIG. 2 shows that engineered expression of Tul4A-C3d by Ft promotes binding to CR2-expressing cells.

To determine whether immunogenicity and protective capacity of iFt LVS immunogens was enhanced by fusion protein expression, C57B/6 mice (8 per group) were immunized and boosted intranasally (i.n.) with $4\times10^7$ iFt LVS (wild type (WT), Tul4A, or Tul4A-C3d-C3d) per mouse on days 0, 14, and 28. Pooled test sera, drawn 12 days after each immunization (#1, 2, and 3), was used in western blot analysis at a 1:500 dilution to probe BHI-grown Ft LVS; normal mouse sera (NMS) and infection-derived immune mouse sera (IMS) were used as controls. On day 42, mice were challenged i.n. with Ft SchuS4. Survival was monitored three times daily for 21 days.

Figure 3:
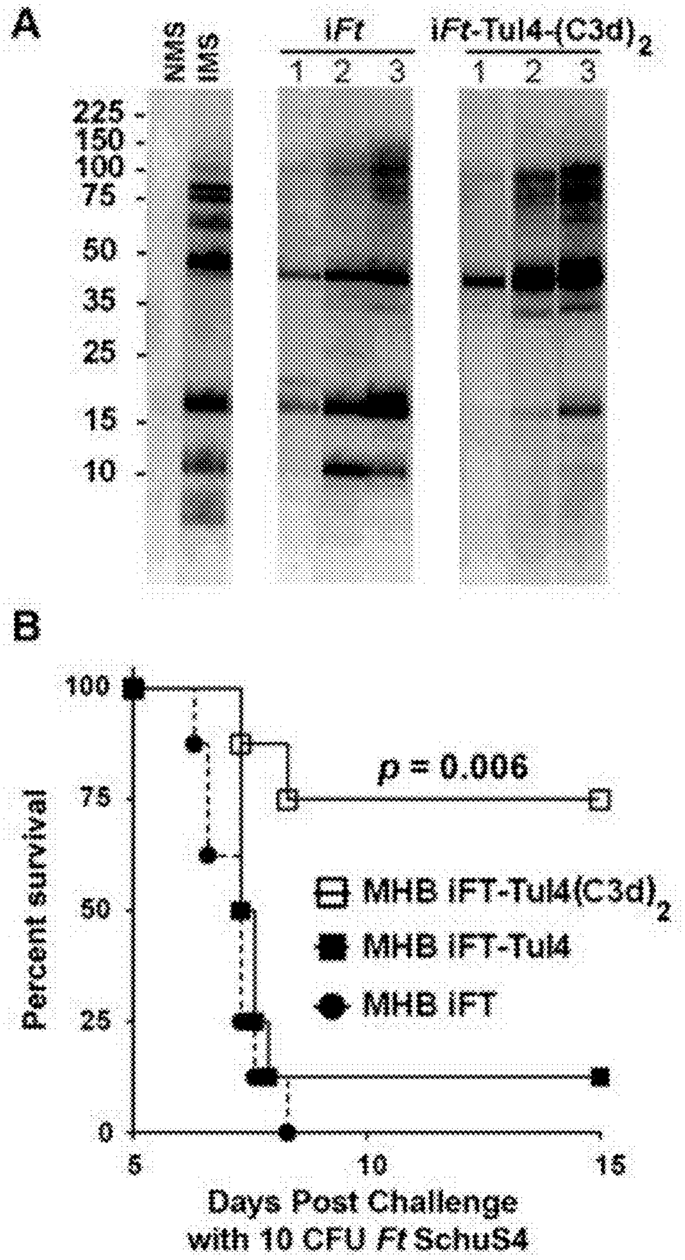
FIG. 3A-B shows that the immunogenicity and protective capacity of iFt LVS immunogens is enhanced by endogenous Tul4A-C3d production. C57B/6 mice (8 per group) were immunized and boosted i.n. with $4\times10^7$ iFt LVS (WT, Tul4A, or Tul4A-C3d-C3d) per mouse on days 0, 14, and 28. A) Pooled test sera, drawn 7 days after each immunization (#1, 2, and 3), was used in western blot analysis at a 1:500 dilution to probe BHI-grown Ft LVS; normal mouse sera (NMS) and infection-derived immune mouse sera (IMS) were used as controls. B) On day 42, mice were challenged i.n. with Ft SchuS4. Survival was monitored three times daily for 21 days. No deaths occurred after day 8; PBS-immunized control mice succumb by day 7.

As shown in the Kaplan-Meier plot in FIG. 3B, no deaths of animals immunized using the fusion protein occurred after day 8; PBS-immunized control mice succumb by day 7. Furthermore, even though overexpression of Tul4A alone conferred some benefit, the survival of animals immunized with iFT Tul4A-C3d-C3d was significantly improved, showing that the immunogenicity and protective capacity of iFt LVS immunogens is enhanced by endogenous Tul4A-C3d production.

Advantages of the Technology

The development of needle-free, mucosal vaccines that do not require exogenous adjuvants is of significant interest to all areas of infectious disease including biodefense. By combining CR2-targeting with TLR2-stimulation the presently disclosed approach addresses this need. Furthermore, as this approach genetically/physically-links the targeting and stimulation moieties to the immunogen, no further manipulation (addition of exogenous targeting moieties, external adjuvants, etc.) of the prepared immunogen is required.

EXAMPLES

Construction of Genetic—Targeting Vectors, pT4C(n)

Using techniques known to those of skill in the art, DNA encoding the surface-exposed lipoprotein (2) Tul4AA (FTT0901) from *Francisella tularensis* (Ft) SchuS4 was PCR-amplified from the bacterium's genome using primers:

```
5'EcoR1SDTul4A:                         (SEQ ID NO: 5)
GAA TTC TGA ATA TTT AAA AAT AGG AGT ATC TAT ATG
and

3' BamH1-Tul4A:                         (SEQ ID NO: 6)
GGA TCC TCA TTA AAT ATT TAT TGA ATC AGA AGC GAT

TAC
```

and subsequently cloned into TOPO PCR 2.1 (Invitrogen). Following validation, the Tul4A insert was sub-cloned as an EcoR1/BamH1 fragment into the same sites of plasmid pF (1) which contains the strong Ft groEL promoter (PgroEL) driving expression of the insert, in this case Tul4A. The PgroEL-Tul4A fusion was amplified from the above plasmid using:

```
forward primer 5'PgroE-KpnBgl2:
                                        (SEQ ID NO: 7)
GGT ACC AGA TCT TTG TAT GGA TTA GTC GAG CTA AAA

AGC
```

-continued

```
and either of the

reverse primers 3' BamH1-Tul4A or
3' BamH1-Tul4A-NS:
                                        (SEQ ID NO: 8)
GGA TCC CCC TCC AAT ATT TAT TGA ATC AGA AGC GAT

 TAC
```

and cloned into TOPO PCR 2.1. The 3' BamH1-Tul4A-NS primer eliminates the native Tul4A stop codon allowing for construction of translational fusions with this lipoprotein which is a known TLR2 agonist (3). These two PgroEL-Tul4A fusions (with and w/o Tul4A stop codons) were digested out of the TOPO PCR 2.1 backbone as Bgl2/XhoI fragments and ligated into the BamH1/Sal1 sites of pBB103 resulting in plasmids pT4 which contains the Tul4A stop codon, and pT4NS which lacks the stop codon and instead contains a GGGS "½ linker" at the C-terminus of Tul4A.

DNA encoding residues 1011 to 1293 (prepro-C3 numbering) of murine C3d was amplified from plasmid pMLC3/7 (ATCC, Manassas, Va.) using the following primers:

```
5' C3d Bgl2:                            (SEQ ID NO: 9)
AGA TCT GGG GGA GGC TCT GGG GAA CAG AAC ATG
and

3' C3d BSSB:                           (SEQ ID NO: 10)
AGA TCT GTC GAC TCA GGA TCC ACC TCC GTT CAA GTC

CTT ATG GTC AGG GAC;
```

the product was cloned into TOPO PCR 2.1. This 5' primer encodes a GGGS (SEQ ID NO: 11) "1/2 linker" at the N-terminus immediately upstream of Gly 1011 of C3d. The 3' primer encodes a GGGS (SEQ ID NO: 11) "1/2 linker" at the C-terminus of C3d immediately downstream of Asn 1293; the primer also contains a BamH1 site followed by a stop codon followed by a Sal1 site followed by a Bgl2 site. Following validation, the c3d insert was sub-cloned as a Bgl2 fragment into the BamH1 site of plasmid pT4NS and a clone in which the c3d insert was similarly oriented to the up-stream Tul4A gene was selected. This plasmid, in which the groEL promoter drives expression of the Tul4A-GGGSGGGS (SEQ ID NO: 12)-C3d-GGGS (SEQ ID NO: 11) fusion protein, was dubbed pT4C1. To construct pT4C2, which contains two tandemly arranged copies of the c3d insert, pT4C1 was digested with BamH1 and Sal1 and ligated to fresh c3d insert as a Bgl2/Sal1 fragment. The same process, albeit starting with pT4C2 instead of pT4C1, was used to generate pT4C3.

Bacteria and Media

Bacteria were grown and maintained in accordance with methods known in the art. Wild-type (WT) *F. tularensis* LVS has been described previously [12], [36], [114]. *F. tularensis* SchuS4, originally isolated from a human case of tularemia, was obtained from the U.S. Army Medical Research Institute for Infectious Diseases (Frederick, Md.). All experiments using SchuS4 were conducted within the Albany Medical College ABSL-3/BSL-3 facility which has been certified by the Center for Disease Control. SchuS4 lysates for protein analysis to be performed outside of this facility were generated by boiling harvested bacteria in 50 mM Tris, pH 8.0 containing 1% SDS followed by sterility testing.

Routine culturing of *F. tularensis* involved streaking aliquots of frozen bacterial glycerol stocks onto Mueller Hinton Chocolate agar plates (Becton, Dickinson and Company (BD), Sparks, Md.) followed by 2-3 days of growth in a humidified chamber maintained at 37° C. Starter cultures were generated by resuspending several isolated colonies in ~100 μl of BHI from which ~50 μl was immediately used to inoculate 3-5 mis of BHI and MHB for ~18 hrs of growth on an orbital shaker operating at 200 rpm and 37° C. Mature starter cultures were used at a 1:100 dilution to inoculate larger volumes (10-50 ml within 125-250 ml Erlenmeyer flasks) of fresh media appropriate for each experiment. Unless stated otherwise, all bacterial cultures used in this work were in mid-log phase (OD600=0.4-0.6). Preparation of MHB and BHI media as well as supplementation of BHI with casamino acids has been described previously [12]. Supplementation of MHB with spermine to 200 μM was performed as described [34].

SDS-PAGE and Western Blot Analysis

Routine SDS-PAGE characterization was used to assess the integrity of the fusion proteins. Samples of *Francisella* [10 μg (~$1\times10^8$ cells)] were mixed with Laemelli sample buffer and boiled for 10 min prior to resolution through 4-12% gradient SDS-PAGE pre-cast gels (Invitrogen). The running buffer was NuPAGE MES SDS buffer from Invitrogen; gels were variously run at 90-160 V. Resolved gels were stained with either coomassie blue (BioRad) or transferred to nitrocellulose membranes. Coomassie-stained gels were scanned into Adobe Photoshop using an HP 2820. Membranes to be probed with mAb were blocked for 15 min with PBS, 0.05% Tween Polvsorbate 20 (TWEEN 20), 1% casein; blots to be probed with polyclonal sera were blocked for 1 hr with PBS, 0.05% TWEEN 20, 2.5% horse serum, 1% casein. Polyclonal sera were applied for 1-2 hr at dilutions ranging from 1:1000 to 1:60,000. Supernatants from mAb-producing hybridomas were applied for overnight (o/n) incubations. The mAb FB11 specific for *F. tularensis* O-antigen (Abcam) was used o/n at a dilution of 1:1000. Blots to be probed multiple times were first probed with mAb prior to stripping and reprobing with polyclonal sera. HRP-conjugated secondary antibodies were used at dilutions ranging from 1:1000 to 1:20,000. Development of the chemiluminescent substrate (SuperSignal West Pico, Pierce, Rockford, Ill.) was visualized using an Alpha Innotech imaging system in movie mode. Densitometric analysis of developed blots was performed on the same system.

Staining of SDS-PAGE Gels

Boiled samples of *F. tularensis* in Laemelli sample buffer (1 ug/ul protein) were de-proteinated with proteinase K (0.4 ug/ul final) at 60° C. for 1 hour and re-boiled prior to resolution through 4-12% gradient SDS-PAGE pre-cast gels (Invitrogen). Each lane was loaded with the de-proteinated material generated from *F. tularensis* lysate containing 10 ug of protein. Carbohydrates were visualized in situ using the Pro-Q Emerald 300 Lipopolysaccharide Gel Stain Kit (Invitrogen) as instructed. Briefly, resolved gels were fixed overnight in 5% acetic acid, 50% methanol. Following two 20 minute washes in 3% acetic acid, the gels were incubated for 30 minutes in oxidizing solution, washed 3 times in 3% acetic acid prior to fluorescent staining of oxidized carbohydrates. After two 20 minute washes in 3% acetic acid, the gels were visualized using a SYBR-green filter and an Alpha Innotech imaging system in movie mode. Following acquisition of the emerald-green signal, gels were de-stained overnight in 3% acetic acid and subsequently stained with SYPRO Ruby fluorescent protein stain (Invitrogen) and visualized using an ethidium bromide filter as above.

Antibody- and Complement-Binding Assays

To assess binding of Ab or complement to the surface of *F. tularensis*, $5\times10^8$ bacteria in 25 ul were mixed with 25 μl of sterile, pre-cleared (10,000×g for 10 min) 0.5×PBS containing 0.1% glucose and either i) 1-5 μl (empirically-determined) of the test Ab/sera (sera were heat-inactivated) for Ab-binding assays or ii) 12.5 μl of intact or heat-inactivated normal mouse sera (for complement-binding assays). To assess the impact of protease inhibitors on Ab-binding, a protease inhibitor cocktail (Sigma, p2714—which includes aprotinin, a plasmin inhibitor) was included in the above Ab mixture. Samples were Incubated at 37° C. for 1.5 hrs (for Ab-binding assays) or for various times (10 min-1 hr) for complement-binding assays. Following incubation, bacteria were pelleted by centrifugation (10,000×g for 10 min) and 45 μl of supernatant was removed. The bacteria were gently resuspended in 1 ml of 0.5×PBS containing 0.1% glucose and pelleted by centrifugation (10,000×g for 10 min) after which the supernatants were aspirated. Following one additional wash, the cells were resuspended to 25 μl in 50 mM Tris pH 8.0 containing protease inhibitors followed by the addition of 25 μl of sample buffer prior to boiling and SDS-PAGE. $1\times10^8$ bacteria per lane were resolved by SDS-PAGE and probed for bound immunoglobulin (IgG or IgM) heavy chain (HC) by western blot. Following development of the Ig HC signals, we re-probed the membranes for total FopA and quantified the data as surface Ab/total FopA and normalized the ratios to the corresponding MHB result. Statistical analysis was performed with the 2-tailed, T-test with Bonferonni corrections when appropriate and significance set at $p<0.05$. As a control, we included a BHI-grown wbtA strain [114] since such strains produce neither LPS OAg nor capsular OAg [30]. Normal mouse serum (NMS) and α-IgIC Ab (directed against a sub-surface protein) were used as control Abs.

Immunization and Challenge

C57Bl6 mice (Taconic, Germantown N.Y.) were maintained and bred in a specific pathogen free environment in the Animal Resource Facility at Albany Medical College. All experiments were conducted using 6-8 week old mice of both sexes and all the animal procedures conformed to the Institutional Animal Care and Use Committee guidelines.

Mice were immunized and boosted i.n. with $4\times10^7$ iFt LVS per mouse on days 0, 14 and 28. Test sera were drawn 12 days after each immunization and pooled; pooled sera was used in western blot analysis at a 1:500 dilution to probe BHI-grown Ft LVS.

On day 42, mice were anesthetized by intra-peritoneal injection of 100 μl of xylazine (20 mg/ml) and ketamine (1 mg/ml) and challenged by intranasal instillation of ~20 CFU of *F. tularensis* SchuS4 in 40 μl of PBS (equally divided between the two nostrils.)

Mice were monitored once-to-thrice daily for 21 days. No deaths occurred after day 8; PBS-immunized control mice succumb by day 7. Survival data are shown in the Kaplan Meier plot of FIG. 3B.

REFERENCES

1. Agostino, M., M. S. Sandrin, P. E. Thompson, W. Farrugia, P. A. Ramsland, and E. Yuriev. 2011. Carbohydrate-mimetic peptides: structural aspects of mimicry and therapeutic implications. Expert Opin Biol Ther 11:211-224.
2. De Temmerman, M. L., J. Rejman, J. Demeester, D. J. Irvine, B. Gander, and S. C. De Smedt. 2011. Particulate vaccines: on the quest for optimal delivery and immune response. Drug Discov Today.
3. Pollard, A. J., R. Galassini, E. M. Rouppe van der Voort, M. Hibberd, R. Booy, P. Langford, S. Nadel, C. Ison, J. S. Kroll, J. Poolman, and M. Levin. 1999. Cellular immune responses to *Neisseria meningitidis* in children. Infect Immun 67:2452-2463.
4. Granoff, D. M., G. R. Moe, M. M. Giuliani, J. Adu-Bobie, L. Santini, B. Brunelli, F. Piccinetti, P. Zuno-Mitchell, S. S. Lee, P. Neri, L. Bracci, L. Lozzi, and R. Rappuoli. 2001. A novel mimetic antigen eliciting protective antibody to *Neisseria meningitidis*. J Immunol 167:6487-6496.
5. Hazlett, K. R., S. D. Caldon, D. G. McArthur, K. A. Cirillo, G. S. Kirimanjeswara, M. L. Magguilli, M. Malik, A. Shah, S. Broderick, I. Golovliov, D. W. Metzger, K. Rajan, T. J. Sellati, and D. J. Loegering. 2008. Adaptation of *Francisella tularensis* to the mammalian environment is governed by cues which can be mimicked in vitro. Infect Immun 76:4479-4488.
6. Schjetne, K. W., K. M. Thompson, N. Nilsen, T. H. Flo, B. Fleckenstein, J. G. Iversen, T. Espevik, and B. Bogen. 2003. Cutting edge: link between innate and adaptive immunity: Toll-like receptor 2 internalizes antigen for presentation to CD4+ T cells and could be an efficient vaccine target. J Immunol 171:32-36.
7. Dempsey, P. W., M. E. Allison, S. Akkaraju, C. C. Goodnow, and D. T. Fearon. 1996. C3d of complement as a molecular adjuvant: bridging innate and acquired immunity. Science 271:348-350.
8. Toapanta, F. R., and T. M. Ross. 2006. Complement-mediated activation of the adaptive immune responses: role of C3d in linking the innate and adaptive immunity. Immunol Res 36:197-210.
9. Kensil, C. R., A. X. Mo, and A. Truneh. 2004. Current vaccine adjuvants: an overview of a diverse class. Front Biosci 9:2972-2988.
10. Bitsaktsis, C., D. B. Rawool, Y. Li, N. V. Kurkure, B. Iglesias, and E. J. Gosselin. 2009. Differential requirements for protection against mucosal challenge with *Francisella tularensis* in the presence versus absence of cholera toxin B and inactivated *F. tularensis*. J Immunol 182:4899-4909.
11. Conlan, J. W. 2011. Tularemia vaccines: recent developments and remaining hurdles. Future Microbiol 6:391-405.
12. McGhee, J. R., and H. Kiyono. 1994. Effective mucosal immunity. Current concepts for vaccine delivery and immune response analysis. Int J Technol Assess Health Care 10:93-106.
13. Areas, A. P., M. L. Oliveira, E. N. Miyaji, L. C. Leite, K. A. Aires, W. O. Dias, and P. L. Ho. 2004. Expression and characterization of cholera toxin B-pneumococcal surface adhesin A fusion protein in *Escherichia coli*: ability of CTB-PsaA to induce humoral immune response in mice. Biochem Biophys Res Commun 321:192-196.
14. Boyaka, P. N., J. W. Lillard, Jr., and J. McGhee. 1999. Interleukin 12 and innate molecules for enhanced mucosal immunity. Immunol Res 20:207-217.
15. McCluskie, M. J., and R. D. Weeratna. 2001. Novel adjuvant systems. Curr Drug Targets Infect Disord 1:263-271.
16. McLendon, M. K., M. A. Apicella, and L. A. Allen. 2006. *Francisella tularensis*: taxonomy, genetics, and Immunopathogenesis of a potential agent of biowarfare. Annu Rev Microbiol 60:167-185.
17. Isherwood, K. E., R. W. Titball, D. H. Davies, P. L. Feigner, and W. J. Morrow. 2005. Vaccination strategies for *Francisella tularensis*. Adv Drug Deliv Rev 57:1403-1414.

18. Conlan, J. W. 2004. Vaccines against *Francisella tularensis*—past, present and future. Expert Rev Vaccines 3:307-314.
19. Karttunen, R., H. M. Surcel, G. Andersson, H. P. Ekre, and E. Herva. 1991. *Francisella tularensis*-induced in vitro gamma interferon, tumor necrosis factor alpha, and interleukin 2 responses appear within 2 weeks of tularemia vaccination in human beings. J Clin Microbiol 29:753-756.
20. Leiby, D. A., A. H. Fortier, R. M. Crawford, R. D. Schreiber, and C. A. Nacy. 1992. In vivo modulation of the murine immune response to *Francisella tularensis* LVS by administration of anticytokine antibodies. Infect Immun 60:84-89.
21. Sjostedt, A., R. J. North, and J. W. Conlan. 1996. The requirement of tumour necrosis factor-alpha and interferon-gamma for the expression of protective immunity to secondary murine tularaemia depends on the size of the challenge inoculum. Microbiology 142 (Pt 6):1369-1374.
22. Rawool, D. B., C. Bitsaktsis, Y. Li, D. R. Gosselin, Y. Lin, N. V. Kurkure, D. W. Metzger, and E. J. Gosselin. 2008. Utilization of Fc receptors as a mucosal vaccine strategy against an intracellular bacterium, *Francisella tularensis*. J Immunol 180:5548-5557.
23. Golovliov, I., M. Ericsson, G. Sandstrom, A. Tarnvik, and A. Sjostedt. 1997. Identification of proteins of *Francisella tularensis* induced during growth in macrophages and cloning of the gene encoding a prominently induced 23-kilodalton protein. Infect Immun 65:2183-2189.
24. Twine, S. M., N. C. Mykytczuk, M. D. Petit, H. Shen, A. Sjostedt, J. Wayne Conlan, and J. F. Kelly. 2006. In vivo proteomic analysis of the intracellular bacterial pathogen, *Francisella tularensis*, isolated from mouse spleen. Biochem Biophys Res Commun 345:1621-1633.
25. Zarrela, T. M., A. Singh, C. Bitsaktsis, T. Rahman, B. Sahay, P. J. Feustel, E. J. Gosselin, T. J. Sellati, and K. R. O. Hazlett. 2011. Host-adaptation of *Francisella tularensis* induces multiple changes to the bacterium's surface-carbohydrates that hinder effectors of innate and adaptive immunity. PLoS One, In Press.
26. Forslund, A. L., K. Kuoppa, K. Svensson, E. Salomonsson, A. Johansson, M. Bystrom, P. C. Oyston, S. L. Michell, R. W. Titball, L. Noppa, E. Frithz-Lindsten, M. Forsman, and A. Forsberg. 2006. Direct repeat-mediated deletion of a type IV pilin gene results in major virulence attenuation of *Francisella tularensis*. Mol Microbiol 59:1818-1830.
27. Kolla, R. V., S. Chintalapati, M. Sabet, E. Santelli, R. C. Liddington, M. David, J. Fierer, D. Guiney, and R. C. Rickert. 2007. Complement C3d conjugation to anthrax protective antigen promotes a rapid, sustained, and protective antibody response. PLoS One 2:e1044.
28. Henson, S. E., D. Smith, S. A. Boackle, V. M. Holers, and D. R. Karp. 2001. Generation of recombinant human C3dg tetramers for the analysis of CD21 binding and function. J Immunol Methods 258:97-109.
29. Cervantes, J. L., S. M. Dunham-Ems, C. J. La Vake, M. M. Petzke, B. Sahay, T. J. Sellati, J. D. Radolf, and J. C. Salazar. 2011. Phagosomal signaling by *Borrelia burgdorferi* in human monocytes involves Toll-like receptor (TLR) 2 and TLR8 cooperativity and TLR8-mediated induction of IFN-beta. Proc Natl Acad Sci USA 108:3683-3688.
30. Pasare, C., and R. Medzhitov. 2004. Toll-like receptors: linking innate and adaptive immunity. Microbes Infect 6:1382-1387.
31. Chiavolini, D., J. Rangel-Moreno, G. Berg, K. Christian, L. Oliveira-Nascimento, S. Weir, J. Alroy, T. D. Randall, and L. M. Wetzler. 2010. Bronchus-associated lymphoid tissue (BALT) and survival in a vaccine mouse model of tularemia. PLoS One 5:e11156.
32. Chiavolini, D., S. Weir, J. R. Murphy, and L. M. Wetzler. 2008. *Neisseria meningitidis* PorB, a Toll-like receptor 2 ligand, improves the capacity of *Francisella tularensis* lipopolysaccharide to protect mice against experimental tularemia. Clin Vaccine Immunol 15:1322-1329.
33. Gregory, S. H., W. H. Chen, S. Mott, J. E. Palardy, N. A. Parejo, S. Heninger, C. A. Anderson, A. W. Artenstein, S. M. Opal, and A. S. Cross. 2010. Detoxified endotoxin vaccine (J5dLPS/OMP) protects mice against lethal respiratory challenge with *Francisella tularensis* SchuS4. Vaccine 28:2908-2915.
34. Malik, M., C. S. Bakshi, B. Sahay, A. Shah, S. A. Lotz, and T. J. Sellati. 2006. Toll-like receptor 2 is required for control of pulmonary infection with *Francisella tularensis*. Infect Immun 74:3657-3662.
35. Lutz, M. B., N. Kukutsch, A. L. Ogilvie, S. Rossner, F. Koch, N. Romani, and G. Schuler. 1999. An advanced culture method for generating large quantities of highly pure dendritic cells from mouse bone marrow. J Immunol Methods 223:77-92.
36. Periasamy, S., A. Singh, B. Sahay, T. Rahman, P. J. Feustel, G. H. Pham, E. J. Gosselin, and T. J. Sellati. 2011. Development of tolerogenic dendritic cells and regulatory T cells favors exponential bacterial growth and survival during early respiratory tularemia. J Leuk Biol, In Press.
37. Klimpel, G. R., T. Eaves-Pyles, S. T. Moen, J. Taormina, J. W. Peterson, A. K. Chopra, D. W. Niesel, P. Carness, J. L. Haithcoat, M. Kirtley, and A. B. Nasr. 2008. Levofloxacin rescues mice from lethal intra-nasal infections with virulent *Francisella tularensis* and induces immunity and production of protective antibody. Vaccine 26:6874-6882.
38. Mara-Koosham, G., J. A. Hutt, C. R. Lyons, and T. H. Wu. 2011. Antibodies contribute to effective vaccination against respiratory infection by type A *Francisella tularensis* strains. Infect Immun 79:1770-1778.
39. Wu, T. H., J. A. Hutt, K. A. Garrison, L. S. Berliba, Y. Zhou, and C. R. Lyons. 2005. Intranasal vaccination induces protective immunity against intranasal infection with virulent *Francisella tularensis* biovar A. Infect Immun 73:2644-2654.
40. Twine, S. M., M. D. Petit, K. M. Fulton, R. V. House, and J. W. Conlan. 2010. Immunoproteomics analysis of the murine antibody response to vaccination with an improved *Francisella tularensis* live vaccine strain (LVS). PLoS One 5:e10000.
41. Savitt, A. G., P. Mena-Taboada, G. Monsalve, and J. L. Benach. 2009. *Francisella tularensis* infection-derived monoclonal antibodies provide detection, protection, and therapy. Clin Vaccine Immunol 16:414-422.
42. Anderson, R. V., D. D. Crane, and C. M. Bosio. 2010. Long lived protection against pneumonic tularemia is correlated with cellular immunity in peripheral, not pulmonary, organs. Vaccine 28:6562-6572.
43. Lyubchenko, T., J. dal Porto, J. C. Gambier, and V. M. Holers. 2005. Coligation of the B cell receptor with complement receptor type 2 (CR2/CD21) using its natural ligand C3dg: activation without engagement of an inhibitory signaling pathway. J Immunol 174:3264-3272.
44. Kwant-Mitchell, A., A. A. Ashkar, and K. L. Rosenthal. 2009. Mucosal innate and adaptive immune responses against herpes simplex virus type 2 in a humanized mouse model. J Virol 83:10664-10676.

45. Ishikawa, F., M. Yasukawa, B. Lyons, S. Yoshida, T. Miyamoto, G. Yoshimoto, T. Watanabe, K. Akashi, L. D. Shultz, and M. Harada. 2005. Development of functional human blood and immune systems in NOD/SCID/IL2 receptor {gamma} chain(null) mice. Blood 106:1565-1573.
46. Van Duyne, R., C. Pedati, I. Guendel, L. Carpio, K. Kehn-Hall, M. Saifuddin, and F. Kashanchi. 2009. The utilization of humanized mouse models for the study of human retroviral infections. Retrovirology 6:76.
47. Shultz, L. D., B. L. Lyons, L. M. Burzenski, B. Gott, X. Chen, S. Chaleff, M. Kotb, S. D. Gillies, M. King, J. Mangada, D. L. Greiner, and R. Handgretinger. 2005. Human lymphoid and myeloid cell development in NOD/LtSz-scid IL2R gamma null mice engrafted with mobilized human hemopoietic stem cells. J Immunol 174: 6477-6489.
48. Wang, M., S. Bregenholt, and J. S. Petersen. 2003. The cholera toxin B subunit directly costimulates antigen-primed CD4+ T cells ex vivo. Scand J Immunol 58:342-349.
49. Cook, E. B., J. L. Stahl, L. Lowe, R. Chen, E. Morgan, J. Wilson, R. Varro, A. Chan, F. M. Graziano, and N. P. Barney. 2001. Simultaneous measurement of six cytokines in a single sample of human tears using microparticle-based flow cytometry: allergics vs. non-allergics. J Immunol Methods 254:109-118.
50. Gosselin, E. J., C. C. Cate, O. S. Pettengill, and G. D. Sorenson. 1986. Immunocytochemistry: its evolution and criteria for its application in the study of epon-embedded cells and tissue. Am J Anat 175:135-160.
51. Gosselin, E. J., J. C. Dennett, G. D. Sorenson, O. S. Pettengill, and C. C. Cate. 1985. Immunocytochemical staining of cytocentrifuge prepared cultured cells: non-specific staining and its elimination. Histochem J 17:847-858.
52. Gosselin, E. J., G. D. Sorenson, J. C. Dennett, and C. C. Cate. 1984. Unlabeled antibody methods in electron microscopy: a comparison of single and multistep procedures using colloidal gold. J Histochem Cytochem 32:799-804.
53. Gosselin, E. J., and D. C. Parker. 1990. Class II MHC molecules and antigen enter the same vesicles during internalization by resting B lymphocytes. Cell. Immunol. 129:404-413.
54. Schulert, G. S., and L. A. Allen. 2006. Differential infection of mononuclear phagocytes by *Francisella tularensis*: role of the macrophage mannose receptor. J Leukoc Biol 80:563-571.

What is claimed is:

1. A nucleic acid that encodes a fusion protein, said nucleic acid comprising a first polynucleotide that consists of the nucleotide sequence of SEQ ID NO: 2; and a second polynucleotide sequence that consists of the nucleotide sequence of SEQ ID NO: 3.

2. A nucleic acid of claim 1 comprising the nucleotide sequence of SEQ ID NO: 1.

3. The nucleic acid of claim 1, wherein said first polynucleotide is linked to said second polynucleotide by a third polynucleotide that encodes a peptide linker.

4. The nucleic acid of claim 1, wherein said first polynucleotide is covalently linked to two or more second polynucleotides in tandem.

5. The nucleic acid of claim 3, wherein said peptide linker is selected from the group consisting of: a glycine linker, a glycine-rich linker and a glycine-serine linker.

6. The nucleic acid of claim 3, wherein the linker is about 3 to about 15 amino acids in length.

7. The nucleic acid of claim 3, wherein the linker is about 5 to about 10 amino acids in length.

8. A vector comprising the nucleic acid of claim 1.

9. An isolated cell comprising the nucleic acid of claim 1.

10. The isolated cell of claim 9, wherein said cell is a bacterial cell.

11. The isolated cell of claim 10, wherein said bacterial cell is selected from the group consisting of *Escherichia coli, Acinetobactor baumannii, Myobacterium tuberculosis, Borrelia burgdorferi, Staphylococcus aureus, Yersinia pestis* and *F. tularensis.*

12. The isolated cell of claim 10, wherein said bacterial cell is selected from the group consisting of *Escherichia coli, Yersinia pestis*, and *F. tularensis.*

13. The isolated cell of claim 10, wherein said bacterial cell is *F. tularensis.*

14. The isolated cell of claim 9, wherein said isolated cell expresses a Tul4A-C3d(n) fusion protein, wherein n=1 to 5.

15. A vaccine comprising an isolated cell of claim 9 and a pharmaceutically acceptable carrier.

16. The vaccine of claim 15, further comprising an adjuvant.

17. A nucleic acid that encodes a fusion protein, the nucleic acid comprising:

(a) a groEL promoter; and (b) the nucleic acid of claim 1.

18. A vector comprising the nucleic acid of claim 17.

19. An isolated bacterial cell comprising the nucleic acid of claim 17.

20. The isolated cell of claim 19, wherein said bacterial cell is selected from the group consisting of *Escherichia coli, Acinetobactor baumannii, Myobacterium tuberculosis, Borrelia burgdorferi, Staphylococcus aureus, Yersinia pestis* and *F. tularensis.*

21. The isolated cell of claim 19, wherein said bacterial cell is selected from the group consisting of *Escherichia coli, Yersinia pestis* and *F. tularensis.*

22. The isolated bacterial cell of claim 19, wherein said cell is *F. tularensis.*

23. A vaccine comprising the bacterial cell of claim 19 and a pharmaceutically acceptable carrier.

24. A method of enhancing the immunogenicity of a bacterial cell, the method comprising: transforming said bacterial cell with the vector of claim 8 and growing the transformed bacterial cell under conditions favorable for expression of the fusion protein by the bacterial cell.

25. A method for immunizing a mammal against tularemia, the method comprising administering the vaccine of claim 15.

26. A method of enhancing the immunogenicity of a bacterial cell, the method comprising: transforming said bacterial cell with the vector of claim 18 and growing the transformed bacterial cell under conditions favorable for expression of the fusion protein by the bacterial cell.

27. A method for immunizing a mammal, the method comprising contacting said mammal with an isolated bacterial cell of claim 19.

* * * * *

SEQUENCE LISTING

```
<160> NUMBER OF SEQ ID NOS: 14

<210> SEQ ID NO 1
<211> LENGTH: 2034
<212> TYPE: DNA
<213> ORGANISM: Artificial Sequence
<220> FEATURE:
<223> OTHER INFORMATION: encodes fusion protein

<400> SEQUENCE: 1

agatctttgt atggattagt cgagctaaaa agctcatatt ttttatattc aaactatata     60

cccttcaagc tttgaaaaat aaacttaatt attatatatg ttatttagct agttttttta    120

attaaagtta aaatcgagag cttgtttgac aaaaaaacaa aaaaatttct tgaaaatttt    180

ttttttgact caatatctag acttgcaaga gcttggaact ttgagattgt tctaagatgc    240

atacaaattc aaaatgctta aacaaaaata atttaacaaa ggagtaagat tgttatgaac    300

attcgtccat tacaagatag agtattagtt cgtcgtgcaa gcgcccaata cgcaaaccgc    360

ctctccccgc gcgttggccg attcattaat gcagctggca cgacaggttt cccgactgga    420

aagcgggcag tgagcgcaac gcaattaatg tgagttagct cactcattag gcaccccagg    480

ctttacactt tatgcttccg gctcgtatgt tgtgtggaat tgtgagcgga taacaatttc    540

acacaggaaa cagctatgac catgattacg ccaagcttgg taccttgaaa attttttttt    600

tgactcaata tctagacttg caagagcttg gaactttgag attgttctaa gatggaattc    660

tgaatattta aaaataggag tatctatatg aaaaaaataa ttgagcttag tcttttatct    720

ttatcaatcg caggtttagc gagctgttct actctagggt taggtggctc tgatgatgca    780

aaagcttcag ctaaagatac tgctgctgct cagacagcta ctactgagca agctgctgct    840

gtatctaagc caactgcaaa agtaagttta aataaacttg gtcaggataa aataaaagca    900

actgtatata caacatacaa taataaccca caaggaagtg taagattaca atggcaggct    960

ccagaaggtt ctaagtgcca tgatacaagc ttcccaatta ctaagtatgc tgagaagaac   1020
```

-continued

```
gataaaactt gggcaactgt aacagttaag caaggtaata acttctgtag cggtaagtgg   1080

acagctaatg tagtttatga caaagaagta atcgcttctg attcaataaa tattggaggg   1140

ggatctgggg gaggctctgg ggaacagaac atgattggca tgacaccaac agtcattgcg   1200

gtacactacc tggaccagac cgaacagtgg gaaaagttcg gcatagagaa gaggcaagag   1260

gccctggagc tcatcaagaa agggtacacc cagcagctgg ccttcaaaca gcccagctct   1320

gcctatgctg ccttcaacaa ccggcccccc agcacctggc tgacagccta cgtggtcaag   1380

gtcttctctc tagctgccaa cctcatcgcc atcgactctc acgtcctgtg tggggctgtt   1440

aaatggttga ttctggagaa acagaagccg gatggtgtct ttcaggagga tgggcccgtg   1500

attcaccaag aaatgattgg tggcttccgg aacgccaagg aggcagatgt gtcactcaca   1560

gccttcgtcc tcatcgcact gcaggaagcc agggacatct gtgaggggca ggtcaatagc   1620

cttcctggga gcatcaacaa ggcaggggag tatattgaag ccagttacat gaacctgcag   1680

agaccataca cagtggccat tgctgggtat gccctggccc tgatgaacaa actggaggaa   1740

ccttacctcg gcaagtttct gaacacagcc aaagatcgga accgctggga ggagcctgac   1800

cagcagctct acaacgtaga ggccacatcc tacgccctcc tggccctgct gctgctgaaa   1860

gactttgact ctgtgccccc tgtagtgcgc tggctcaatg agcaaagata ctacggaggc   1920

ggctatggct ccacccaggc taccttcatg gtattccaag ccttggccca atatcaaaca   1980

gatgtccctg accataagga cttgaacgga ggtggatcct gagtcgacag atct          2034


<210> SEQ ID NO 2
<211> LENGTH: 447
<212> TYPE: DNA
<213> ORGANISM: Francisella tularensis

<400> SEQUENCE: 2

atgaaaaaaa taattgagct tagtctttta tctttatcaa tcgcaggttt agcgagctgt     60

tctactctag ggttaggtgg ctctgatgat gcaaaagctt cagctaaaga tactgctgct    120

gctcagacag ctactactga gcaagctgct gctgtatcta agccaactgc aaaagtaagt    180

ttaaataaac ttggtcagga taaaataaaa gcaactgtat atacaacata caataataac    240

ccacaaggaa gtgtaagatt acaatggcag gctccagaag gttctaagtg ccatgataca    300

agcttcccaa ttactaagta tgctgagaag aacgataaaa cttgggcaac tgtaacagtt    360

aagcaaggta ataacttctg tagcggtaag tggacagcta atgtagttta tgacaaagaa    420

gtaatcgctt ctgattcaat aaatatt                                        447


<210> SEQ ID NO 3
<211> LENGTH: 849
<212> TYPE: DNA
<213> ORGANISM: Mus musculus

<400> SEQUENCE: 3

ggggaacaga acatgattgg catgacacca acagtcattg cggtacacta cctggaccag     60

accgaacagt gggaaaagtt cggcatagag aagaggcaag aggccctgga gctcatcaag    120

aaagggtaca cccagcagct ggccttcaaa cagcccagct ctgcctatgc tgccttcaac    180

aaccggcccc ccagcacctg gctgacagcc tacgtggtca aggtcttctc tctagctgcc    240

aacctcatcg ccatcgactc tcacgtcctg tgtggggctg ttaaatggtt gattctggag    300

aaacagaagc cggatggtgt ctttcaggag gatgggcccg tgattcacca agaaatgatt    360

ggtggcttcc ggaacgccaa ggaggcagat gtgtcactca cagccttcgt cctcatcgca    420
```

-continued ctgcaggaag ccagggacat ctgtgagggg caggtcaata gccttcctgg gagcatcaac 480
aaggcagggg agtatattga agccagttac atgaacctgc agagaccata cacagtggcc 540
attgctgggt atgccctggc cctgatgaac aaactggagg aaccttacct cggcaagttt 600
ctgaacacag ccaaagatcg gaaccgctgg gaggagcctg accagcagct ctacaacgta 660
gaggccacat cctacgccct cctggccctg ctgctgctga aagactttga ctctgtgccc 720
cctgtagtgc gctggctcaa tgagcaaaga tactacggag gcggctatgg ctccacccag 780
gctaccttca tggtattcca agccttggcc caatatcaaa cagatgtccc tgaccataag 840
gacttgaac 849

<210> SEQ ID NO 4
<211> LENGTH: 5687
<212> TYPE: DNA
<213> ORGANISM: Artificial Sequence
<220> FEATURE:
<223> OTHER INFORMATION: synthetic construct

<400> SEQUENCE: 4
aagctttaat gcggtagttt atcacagtta aattgctaac gcagtcaggc accgtgtatg 60
aaatctaaca atgcgctcat cgtcatcctc ggcaccgtca ccctggatgc tgtaggcata 120
ggcttggtta tgccggtact gccgggcctc ttgcgggata tcgtccattc cgacagcatc 180
gccagtcact atggcgtgct gctagcgcta tatgcgttga tgcaatttct atgcgcaccc 240
gttctcggag cactgtccga ccgctttggc cgccgcccag tcctgctcgc ttcgctactt 300
ggagccacta tcgactacgc gatcatggcg accacacccg tcctgtggat cctaacatcc 360
ggataggtga attcacatag tcgactgatt ggtaccatct caagaagatc cctgcaggtg 420
ccttgtacag cgttgcgatt ttcgttcgtg aatacatgct ataataacta taactaataa 480
cgtaacgtga ctggcaagag atatttttaa aacaatgaat aggtttacac ttactttagt 540
tttatggaaa tgaaagatca tatcatatat aatctagaat aaaattaact aaaataatta 600
ttatctagat aaaaaattta gaagccaatg aaatctataa ataaactaaa ttaagtttat 660
ttaattaaca actatggata taaaataggt actaatcaaa atagtgagga ggrbsatata 720
tttgstarta atacatacga acaaattaat aaagtgaaaa aaatacttcg gaaacattta 780
aaaaataacc ttattggtac ttacatgttt ggatcaggag ttgagagtgg actaaaacca 840
aatagtgatc ttgacttttt agtcgtcgta tctgaaccat tgacagatca aagtaaagaa 900
atacttatac aaaaaattag acctatttca aaaaaaatag gagataaaag caacttacga 960
tatattgaat taacaattat tattcagcaa gaaatggtac cgtggaatca tcctcccaaa 1020
caagaattta tttatggaga atggttacaa gagctttatg aacaaggata cattcctcag 1080
aaggaattaa attcagattt aaccataatg ctttaccaag caaaacgaaa aaataaaaga 1140
atatacggaa attatgactt agaggaatta ctacctgata ttccattttc tgatgtgagg 1200
agagccatta tggattcgtc agaggaatta atagataatt atcaggatga tgaaaccaac 1260
tctatattaa ctttatgccg tatgatttta actatggaca cgggtaaaat cataccaaaa 1320
gatattgcgg gaaatgcagt ggctgaatct tctccattag aacataggga gagaattttg 1380
ttagcagttc gtagttatct tggagagaat attgaatgga ctaatgaaaa tgtaaattta 1440
actataaact atttaaataa cagattaast aaaaattata aaaaaattga aaaaatggtg 1500
gaaacacctt aaggtatacc atatgcccgg ggtcctcgag accatgggca aatattatac 1560

-continued gcaaggcgac aaggtgctga tgccgctggc gattcaggtt catcatgccg tttgtgatgg 1620
cttccatgtc ggcagaatgc ttaatgaatt acaacagtac tgcgatgagt ggcagggcgg 1680
ggcgtaattt ttttaaggca gttattggtg cccttaaacg cctggtgcta cgcctgaata 1740
agtgataata agcggatgaa tggcagaaat tcgaaagcaa attcgacccg gtcgtcggtt 1800
cagggcaggg tcgttaaata gccgcttatg tctattgctg gtttaccggt ttattgacta 1860
ccggaagcag tgtgaccgtg tgcttctcaa atgcctgagg ccagtttgct caggctctcc 1920
ccgtggaggt aataattgac gatatgatca tttattctgc ctcccagagc ctgataaaaa 1980
cggtgaatcc gttagcgagg tgccgccggc ttccattcag gtcgaggtgg cccggctcca 2040
tgcaccgcga cgcaacgcgg ggaggcagac aaggtatagg gcggcgccta caatccatgc 2100
caacccgttc catgtgctcg ccgaggcggc ataaatcgcc gtgacgatca gcggtccagt 2160
gatcgaagtt aggctggtaa gagccgcgag cgatccttga agctgtccct gatggtcgtc 2220
atctacctgc ctggacagca tggcctgcaa cgcgggcatc ccgatgccgc cggaagcgag 2280
aagaatcata atggggaagg ccatccagcc tcgcgtcgcg aacgccagca agacgtagcc 2340
cagcgcgtcg gccgccatgc cggcgataat ggcctgcttc tcgccgaaac gtttggtggc 2400
gggaccagtg acgaaggctt gagcgagggc gtgcaagatt ccgaataccg caagcgactt 2460
ctcatgtttg acagcttatc atcgataagc ttatgaagaa acagcctatc ttatgagaag 2520
catgaacaac tataagagac tacaaaattc tattgatgaa gtagaatctg gtttagctat 2580
ccaaaaagag ttgattgaag aatgatactt tcttggtcaa ctaatgcttg ggaagattat 2640
ctatattggc aaagcataga taagaaaaag ctaaaacgga ttaatttgct aatcaaagac 2700
attatgagaa atcactttga gggattagga gagcctgaac ctttgaagca taatttctct 2760
ggttattggt ctagcgatga taagctgtca aacatgagaa ttacaactta tatcgtatgg 2820
ggctgacttc aggtgctaca tttgaagaga taaattgcac tgaaatctag aaatatttta 2880
tctgattaat aagatgatct tcttgagatc gttttggtct gcgcgtaatc tcttgctctg 2940
aaaacgaaaa aaccgccttg cagggcggtt tttcgaaggt tctctgagct accaactctt 3000
tgaaccgagg taactggctt ggaggagcgc agtcaccaaa acttgtcctt tcagtttagc 3060
cttaaccggc gcatgacttc aagactaact cctctaaatc aattaccagt ggctgctgcc 3120
agtggtgctt ttgcatgtct ttccgggttg gactcaagac gatagttacc ggataaggcg 3180
cagcggtcgg actgaacggg gggttcgtgc atacagtcca gcttggagcg aactgcctac 3240
ccggaactga gtgtcaggcg tggaatgaga caaacgcggc cataacagcg gaatgacacc 3300
ggtaaaccga aaggcaggaa caggagagcg cacgagggag ccgccagggg gaaacgcctg 3360
gtatctttat agtcctgtcg ggtttcgcca ccactgattt gagcgtcaga tttcgtgatg 3420
cttgtcaggg gggcggagcc tatggaaaaa cggctttgcc gcggccctct cacttccctg 3480
ttaagtatct tcctggcatc ttccaggaaa tctccgcccc gttcgtaagc catttccgct 3540
cgccgcagtc gaacgaccga gcgtagcgag tcagtgagcg aggaagcgga atatatcctg 3600
tatcacatat tctgctgacg caccggtgca gcctttttc tcctgccaca tgaagcactt 3660
cactgacacc ctcatcagtg ccaacatagt aagccagtat acactccgct agcgctgatg 3720
tccggcggtg cttttgccgt tacgcaccac cccgtcagta gctgaacagg agggacagaa 3780
gcttgtcagt ctcttctcta gaaatgtacc aaattttacc tattttagga tacttttcat 3840
gaagctcttc tattttttccc cagtccttta atagtctacc tttagagtct cgtaaatagt 3900
tatctttgtg acaggggcct cttttatctt ttttaatgta actatatgtt attccaacgt 3960

```
cactattact attatccaaa tctttttag catgccagta agaactttca taacttaact   4020

ctatctttcg acctctttga tatacaacaa taaagctata gccagtagta acaacctgtt   4080

ttacttttgt taaatctatt aacttcttat ttattttttt atgttttttt gaaaatttaa   4140

atatttctat attcattcct acacttcctc aaatccaaat ggtagcttat gattctcttc   4200

tggtttcttt tctaattttt ttatatttgc aataaaaact ctttttctat ctttgatttt   4260

tttattgtcc caattcctcc aagtatcatc acaaaccctt tcaatatcat gtaaatgatg   4320

atgtctaaat attgatctga cataatacag atctaggtct agttcatcac ttaacacaac   4380

ttctctaagt ctttcagatg cttcgattgg tatgtaatcc tctttatttt tagtatctaa   4440

aagcttttgc ttaaattctt cttctgtctc tgctacctta ctaactgtaa acttgatatt   4500

tgtaatctta cgaccatgtt ttctgtgatg atccttgtca tcataggtta caaaaatatc   4560

cgataattga ttaatctctt ctagtgctgg taataggaac ttatttttaa aatttgaata   4620

tctgttgctg taacttttag gtaaatcaaa atcattaatc atatcatcga catacaatac   4680

gcaatcaact atattagcat accctgcttg ttcgcctaat ttgcttttga gaagtaagta   4740

taatctgctt gaatacttac ttttaaatga aaatagtaac tgtctttctg ctttagtaaa   4800

gtactcttgt agttgtatca tgtgtggcat taatgaccaa tgaaactcgc aaattaaagc   4860

actgctttta gggtctgctt caatatatgc aaaccagtta gctatcttcg tttgttcttt   4920

attcagccat actggcttag acattattga gtgcattaat tgcttcaatc tcactctgtt   4980

atgcttaacc cctgtagctt tttcaagatc agataggctt atcttatacc tgtgaaactc   5040

tttatcttct cttttaacca ttgaggcaac taagaatatt aagttttgtt cttcttttgt   5100

aaggctatac tttcctgcaa caagagtatt agacatagct atttctttgc cagcatttac   5160

atttttaact tctttcatag aactagagtc attatctcga tatacaaatt ctataaaact   5220

tctattagta aaacaactac ttcataaaaa aaagtagttt taacgataca aaaagtagtt   5280

ttaaattcaa aaagtgatac aaaaagtagt tttaaattca aaaagtgata caaaaagtag   5340

ttttaaattt tttaaaaaag tgcttcaaag ccttatgtag caatacttac agaggattaa   5400

aaaaaaatct gacaatatat aaagagaata tataaagaga atatcttagg ggattttaaa   5460

aaaatcccac agactcaaag actttttga ctttttaaat cctagaaact atactttaag   5520

tacttattta agtacatgga tttagattat gcaaaccgtt aattattcaa cttttagaaa   5580

tgaactatct gattcaatgg atagagtaac aaaaaatcat agtcctatga ttgtaactag   5640

aggttcaaaa aaagaagcag ttgttatgat gtcgttagag gatttta                 5687
```

<210> SEQ ID NO 5
<211> LENGTH: 36
<212> TYPE: DNA
<213> ORGANISM: Artificial Sequence
<220> FEATURE:
<223> OTHER INFORMATION: synthetic primer

<400> SEQUENCE: 5

```
gaattctgaa tatttaaaaa taggagtatc tatatg                                36
```

<210> SEQ ID NO 6
<211> LENGTH: 39
<212> TYPE: DNA
<213> ORGANISM: Artificial Sequence
<220> FEATURE:
<223> OTHER INFORMATION: synthetic primer

<400> SEQUENCE: 6
ggatcctcat taaatattta ttgaatcaga agcgattac 39

<210> SEQ ID NO 7
<211> LENGTH: 39
<212> TYPE: DNA
<213> ORGANISM: Artificial Sequence
<220> FEATURE:
<223> OTHER INFORMATION: syntheitc primer

<400> SEQUENCE: 7
ggtaccagat ctttgtatgg attagtcgag ctaaaaagc 39

<210> SEQ ID NO 8
<211> LENGTH: 39
<212> TYPE: DNA
<213> ORGANISM: Artificial Sequence
<220> FEATURE:
<223> OTHER INFORMATION: synthetic primer

<400> SEQUENCE: 8
ggatccccct ccaatattta ttgaatcaga agcgattac 39

<210> SEQ ID NO 9
<211> LENGTH: 33
<212> TYPE: DNA
<213> ORGANISM: Artificial Sequence
<220> FEATURE:
<223> OTHER INFORMATION: synthetic primer

<400> SEQUENCE: 9
agatctgggg gaggctctgg ggaacagaac atg 33

<210> SEQ ID NO 10
<211> LENGTH: 51
<212> TYPE: DNA
<213> ORGANISM: Artificial Sequence
<220> FEATURE:
<223> OTHER INFORMATION: synthetic primer

<400> SEQUENCE: 10
agatctgtcg actcaggatc cacctccgtt caagtcctta tggtcaggga c 51

<210> SEQ ID NO 11
<211> LENGTH: 4
<212> TYPE: PRT
<213> ORGANISM: Artificial Sequence
<220> FEATURE:
<223> OTHER INFORMATION: synthetic linker peptide

<400> SEQUENCE: 11

Gly Gly Gly Ser
1

<210> SEQ ID NO 12
<211> LENGTH: 8
<212> TYPE: PRT
<213> ORGANISM: Artificial Sequence
<220> FEATURE:
<223> OTHER INFORMATION: synthetic linker peptide

<400> SEQUENCE: 12

Gly Gly Gly Ser Gly Gly Gly Ser
1 5

-continued

```
<210> SEQ ID NO 13
<211> LENGTH: 6
<212> TYPE: PRT
<213> ORGANISM: Artificial Sequence
<220> FEATURE:
<223> OTHER INFORMATION: synthetic linker peptide

<400> SEQUENCE: 13

Gly Gly Gly Asn Gly Gly
1               5


<210> SEQ ID NO 14
<211> LENGTH: 4
<212> TYPE: PRT
<213> ORGANISM: Artificial Sequence
<220> FEATURE:
<223> OTHER INFORMATION: synthetic linker peptide

<400> SEQUENCE: 14

Gly Gly Gly Gly
1
```